United States Patent
Srour et al.

(10) Patent No.: US 10,026,993 B2
(45) Date of Patent: Jul. 17, 2018

(54) METHOD FOR SYNTHESIZING IONIC LIQUIDS HAVING A CARBONATE FUNCTIONAL GROUP AND IONIC LIQUIDS THUS OBTAINED

(71) Applicants: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR); UNIVERSITE CLAUDE BERNARD LYON 1, Villeurbanne (FR); CPE LYON, Villeurbanne (FR)

(72) Inventors: Hassan Srour, Villeurbanne (FR); Helene Rouault, Le Versoud (FR); Catherine Santini, Collonges Mont D'or (FR)

(73) Assignees: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR); UNIVERSITE CLAUDE BERNARD LYON 1, Villeurbanne (FR); CPE LYON, Villeurbanne (FR)

( * ) Notice: Subject to any disclaimer, the term of this patent is extended or adjusted under 35 U.S.C. 154(b) by 0 days.

(21) Appl. No.: 14/767,407

(22) PCT Filed: Feb. 10, 2014

(86) PCT No.: PCT/EP2014/052518
§ 371 (c)(1),
(2) Date: Aug. 12, 2015

(87) PCT Pub. No.: WO2014/124892
PCT Pub. Date: Aug. 21, 2014

(65) Prior Publication Data
US 2015/0380771 A1  Dec. 31, 2015

(30) Foreign Application Priority Data
Feb. 13, 2013 (FR) .................... 13 51205

(51) Int. Cl.
*C07D 233/60* (2006.01)
*H01M 10/0569* (2010.01)
*C07C 303/40* (2006.01)
*C07C 213/06* (2006.01)
*H01M 10/052* (2010.01)
*C07C 311/48* (2006.01)
*H01M 10/0525* (2010.01)
*H01M 4/587* (2010.01)

(52) U.S. Cl.
CPC ....... *H01M 10/0569* (2013.01); *C07C 213/06* (2013.01); *C07C 303/40* (2013.01); *C07C 311/48* (2013.01); *C07D 233/60* (2013.01); *H01M 10/052* (2013.01); *H01M 10/0525* (2013.01); *H01M 4/587* (2013.01); *H01M 2300/0028* (2013.01); *H01M 2300/0045* (2013.01); *Y02P 20/582* (2015.11)

(58) Field of Classification Search
CPC .................................................. C07D 233/60
See application file for complete search history.

(56) References Cited

U.S. PATENT DOCUMENTS

2006/0035137 A1  2/2006 Maruo et al.
2012/0107697 A1  5/2012 Roh et al.

FOREIGN PATENT DOCUMENTS

| EP | 1 548 866 | 6/2005 |
| EP | 2 450 999 | 5/2012 |
| JP | 4478790 | 6/2010 |

OTHER PUBLICATIONS

International Search Report dated Apr. 7, 2014 in PCT/EP2014/052518 filed Feb. 10, 2014.
Nguyen, D. Q., et al., "Synthesis and Characterization of Quaternary Ammonium-based Ionic Liquids Containing an Alkyl Carbonate Group", Alkyl Carbonate-functionalized Ionic Liquids, Bull. Korean Chem. Soc., vol. 28, No. 12, pp. 2299-2302, XP009117677, 2007.

*Primary Examiner* — Rebecca L Anderson
(74) *Attorney, Agent, or Firm* — Oblon, McClelland, Maier & Neustadt, L.L.P.

(57) ABSTRACT

The present invention relates to a method for synthesizing ionic liquids comprising a carbonate functional group characterized in that it comprises a step of reaction A without addition of lithium between a first reactant selected among an imidazolium, a pyrrolidinium or an ammonium and a second reactant being a methyl formate imidazolium. The first reactant is an imidazolium alcohol, a pyrrolidinium alcohol or an ammonium alcohol salt, the anion of which is NTf2. The second reactant is a chloromethyl formate imidazolium.
The application of this method will be found in the field of green chemistry and more specifically in the production of ionic liquids which can be used in lithium batteries with a graphite electrode.

13 Claims, 2 Drawing Sheets

METHOD FOR SYNTHESIZING IONIC LIQUIDS HAVING A CARBONATE FUNCTIONAL GROUP AND IONIC LIQUIDS THUS OBTAINED

The present invention relates to a method for synthesizing ionic liquids having a carbonate functional group and the ionic liquids thus obtained.

Ionic liquids are salts having a melting temperature below 100° C.

Ionic liquids are composed of organic cations and (in) organic anions. They have many advantages and have, in recent years, experienced a particular enthusiasm in various fields of chemistry among which green solvents, catalysis or even separation.

Ionic liquids obtained using the present method may find applications in enzymatic catalysis or in biomass dissolution.

Ionic liquids may also be used as electrolytes in lithium batteries. They are considered safer because of their low volatility and flammability.

Graphite electrodes for lithium-based batteries have simultaneously been developed. Such electrodes have the advantage of being manufactured at low cost and being more environmentally-friendly than the electrodes of the prior art.

However, the ionic liquids known to date cannot be used with such particular graphite electrodes since the lithium ions in the battery cannot be inserted between the graphite sheets. Additives such as vinylene carbonate (VC) are thus added to form a solid electrolyte interface (SEI) on the graphite electrode thereby extending the service life of the batteries. However, the necessary additives are expensive volatile organic solvents and this limits the interest of ionic liquids in the field of lithium batteries.

A publication, Nguyen, Buul. Korean Chem. Soc. 2007 28, 2299, presented ionic liquids comprising a carbonate functional group. This type of ionic liquid thus no longer requires the addition of additive to be used in lithium batteries with a graphite electrode. The synthesis of such ionic liquids involves a step of anion metathesis involving a lithium salt. The ionic liquids obtained do not, however, have satisfactory properties for use as electrolyte in batteries. The authors have identified an interaction between the carbonate functional group and the lithium salt, using infrared spectroscopy. Such interaction implies the presence of lithium in the final ionic liquid. Such ionic liquids cannot be used as electrolytes in lithium batteries.

A need therefore exists for a method for synthesizing ionic liquid having a carbonate functional group, which solves all or part of the disadvantages mentioned above.

For this purpose, the present invention relates to a method for synthesizing ionic liquids comprising a carbonate functional group, with the method comprising a step of reaction A without addition of lithium between a first reactant selected among an imidazolium, a pyrrolidinium or an ammonium and a second reactant being a methyl formate imidazolium.

The reaction of synthesis of the ionic liquid according to the invention involves no lithium which makes it possible to obtain a pure ionic liquid comprising a carbonate functional group. The resulting ionic liquid can thus be directly used as an electrolyte, specifically in lithium batteries having at least one graphite electrode.

The ionic liquid with a synthesized carbonate functional group contains no lithium. It contains no halide either.

According to an advantageous embodiment, the method according to the invention makes it possible to recycle the secondary product obtained during the reaction A when synthesizing the ionic liquid. The secondary product is recycled by reacting for said reaction A. The method thus generates no waste to be treated.

The present method is quick and inexpensive to implement.

Further aims and advantages of the invention will appear from the following description, which discloses an illustrative but not restrictive embodiment of the invention.

According to preferred but not restrictive embodiments, the invention is such that:
- the first reactant is an imidazolium, pyrrolidinium or ammonium alcohol;
- the first reactant is an imidazolium alcohol, alcohol pyrrolidinium or ammonium alcohol salt, the anion of which is bis(trifluoromethanesulfonyl)imide NTf 2; the step of reaction A results in two products, with a main product being an ionic liquid comprising a carbonate functional group and a secondary product being a methyl imidazolium;
- it comprises a further step of recycling, by Hoffmann reaction, the secondary product methyl imidazolium into an imidazolium alcohol, forming the first reactant of the reaction A.
- methyl imidazolium reacts with 2-chloro-1-ethanol to form 1-ethanol-3-methyl imidazolium chloride;
- the chlorine of 1-ethanol-3-methyl imidazolium chloride is substituted by NTf2, by reaction with LiNtf2;
- the step of reaction A is executed at ambient temperature in an acetonitrile-based solution in argon atmosphere; preferably in acetonitrile;
- the second reactant is a chloromethyl formate imidazolium.
- the second reactant is obtained by reaction between 1-methylimidazole and methylchloroformate.
- the reaction step is executed at 0° C. in an acetonitrile-based solution for 2 hours; preferably in acetonitrile;
- the second reactant obtained by reaction between 1-methylimidazole and methylchloroformate is directly mixed with the first reactant of reaction A.

According to another aspect, the invention relates to an ionic liquid comprising a carbonate functional group obtained using the method of the invention above.

According to another aspect, the invention relates to a lithium battery and at least one graphite electrode comprising an ionic liquid according to the invention. Advantageously, the ionic liquid is used as an electrolyte in the battery.

As generally known by the persons skilled in the art, lithium battery generally consists of:
- two electrodes, i.e. one positive electrode and one negative electrode. The positive electrode generally comprises, as the electrochemically active material, lithium intercalation materials such as lamellar oxides of transition metals containing lithium, olivines (LiFeP04) or spinels (e.g. LiNiO, 5Mn1, 5O4 spinel). The negative electrode generally comprises, as the electrochemically active material, intercalation materials such as graphite carbon (Cgr).
- current collectors, typically made of copper for the negative electrode, or aluminum for the positive electrode, which enable the electrons to circulate, and hence the electron conduction, in the external circuit;
- an ionic liquid electrolyte comprising a lithium salt wherein ionic conduction occurs, which ensures the passage of lithium ions from one electrode to the other.

The appended drawings are provided as examples and are non-exhaustive depictions of the invention. They only show one embodiment of the invention and help it to be understood clearly.

Figure 1:
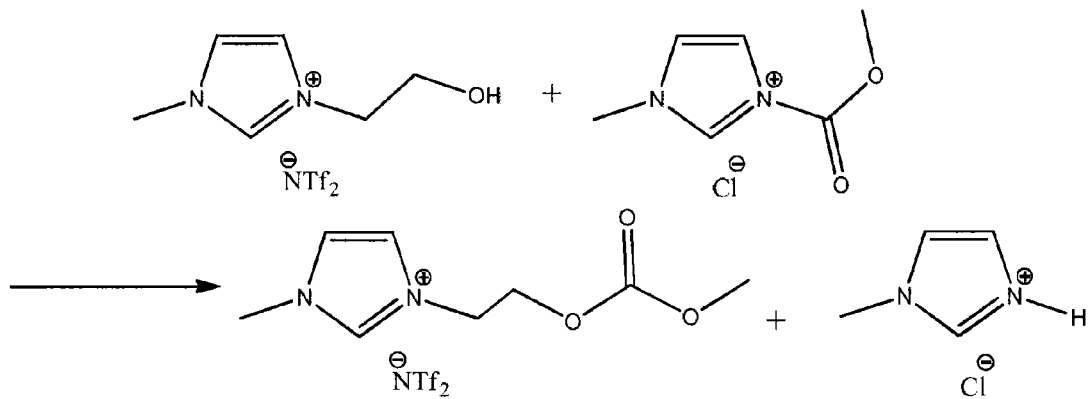
FIG. 1 illustrates an example of the step of reaction A of the synthesis method according to the invention.
Figure 2:
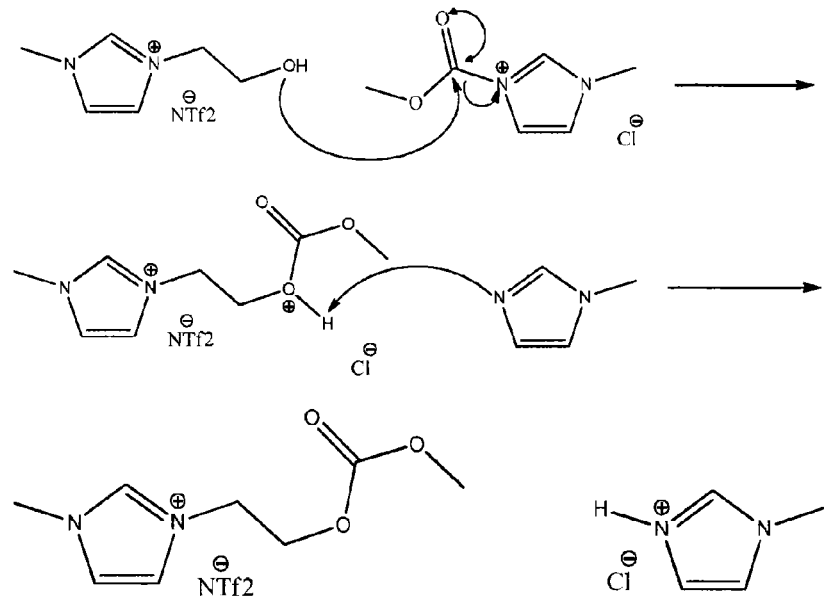
FIG. 2 illustrates the mechanism of the reaction A of the synthesis method according to the invention.
Figure 3:
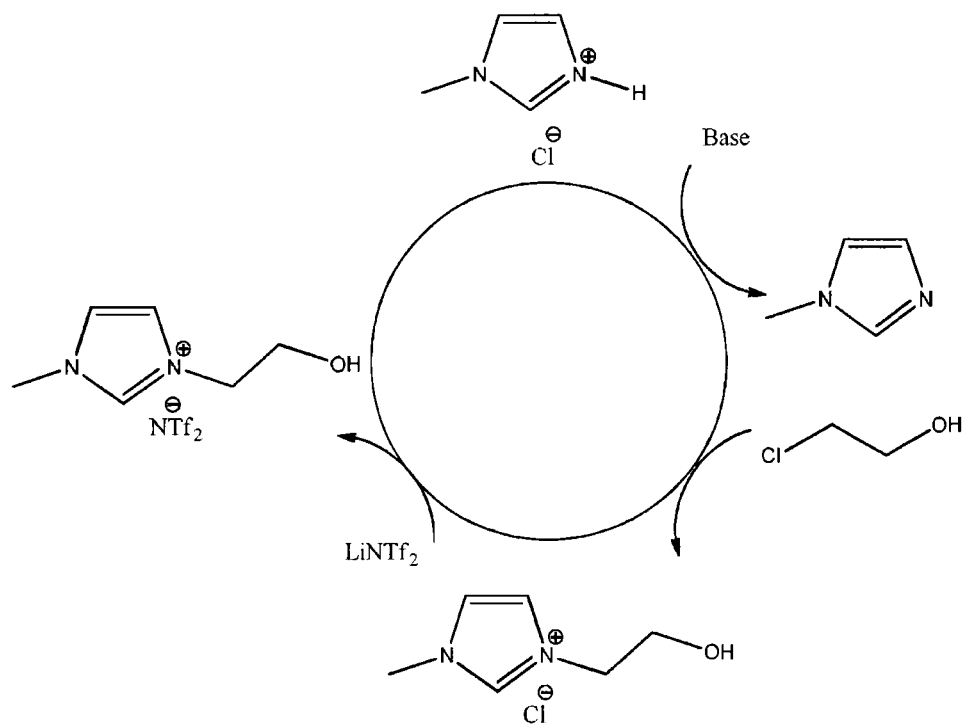
FIG. 3 illustrates an exemplary step of recycling the secondary product resulting from the reaction A of the method according to the invention.
Figure 4:
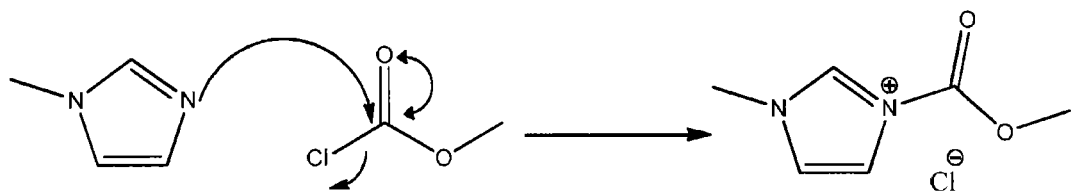
FIG. 4 illustrates the mechanism of the reaction A of the synthesis of the second reactant of the method according to the invention.

According to the invention, the method for synthesizing an ionic liquid comprises a reaction A between two reactants 1, 2.

The first reactant is selected from imidazolium, pyrrolidinium or ammonium according to the type of ionic liquid desired to be synthesized. The first reactant 1 is advantageously an imidazolium, pyrrolidinium or ammonium alcohol. The first reactant is in the form of a salt the anion of which is bis(trifluoromethanesulfonyl)imide (also called NTf2 or TFSI), and the cation of which is imidazolium, pyrrolidinium or ammonium. The anion NTf2 makes the ionic liquid a hydrophobic characteristic, which makes synthesis and purification thereof easier.

By way of non limiting example, the first reactant 1 is 1-ethanol-3-methylimidazolium bis(trifluoromethanesulfonyl)imide, also called C1C2OHIm-NTf2. The first reactant is directly commercially available.

The second reactant is methyl formate imidazolium. The second reactant is preferably chloromethyl formate imidazolium. For example, the second reactant 2 is 1-methyl-3-methylformateImidazolium chloride. The second reactant is advantageously obtained by a step of reaction between methyl-imidazole and methylchloroformate. The reaction advantageously takes place at 0° C. in acetonitrile. The reaction lasts for about 2 hours.

Preferably, once the second reactant has been synthesized, the first reactant is directly mixed with the second reactant without separation thereof.

This greatly facilitates the synthesizing method according to the invention.

The step of reaction A between the first reactant and the second reactant enables the direct synthesis of the ionic liquid having at least one carbonate functional group. This step of reaction A is advantageously carried out in acetonitrile at room temperature, more specifically between 18° C. and 25° C. in argon atmosphere.

For example, the ionic liquids which can be obtained using the method according to the invention are, as for the cation:

1-[2-(methoxycarbonyloxy)ethyl]-3-methylimidazolium
1[2-(ethoxycarbonyloxy)ethyl]-3-methylimidazolium
1[2-(propoxycarbonyloxy)ethyl]-3-methylimidazolium
1-[2-(isopropoxycarbonyloxy)ethyl]-3-methylimidazolium
N-[2-(methoxycarbonyloxy)ethyl]-N'-methylpyrrolidinium
N-[2-(ethoxycarbonyloxy)ethyl]-N'-methylpyrrolidinium
N-[2-(propoxycarbonyloxy)ethyl]-N'-methylpyrrolidinium
N-[2-(isopropoxycarbonyloxy)ethyl]-N'-methylpyrrolidinium
N-trimethyl-N-2-[(methoxycarbonyloxy)ethyl]ammonium
N-trimethyl-N-2-[(ethoxycarbonyloxy)ethyl]ammonium
N-trimethyl-N-2-[(propoxycarbonyloxy)ethyl]ammonium
N-trimethyl-N-2-[(isopropoxycarbonyloxy)ethyl]ammonium;

The associated anion is bis(trifluoromethanesulfonyl)imide.

The step of reaction A leads to two products, among which a main product which is the ionic liquid comprising at least one carbonate functional group and a secondary product.

The ionic liquid obtained has a carbonate functional group. Advantageously, it is halide-free. As a matter of fact, chlorine in the second reactant is the anion of the secondary product. Besides, the step of reaction A involves no reactant containing lithium. The synthesis method according to the invention is executed without lithium. There is no coordination of lithium or halide with the carbonate functional group.

The secondary product contains chloro-imidazolium from the second reactant. For example, the secondary product is methyl imidazolium chloride.

The method of the invention also has the advantage of making it possible to recycle the secondary product into a reactant, specifically the first reactant. Recycling the secondary product of the step of reaction A is obtained by Hoffmann reaction. Such reaction cycle is described in patent application WO 01/77081. The step of recycling is preferably carried out between the secondary product and 2-chloro-1-ethanol. The product of this reaction includes a halide which is advantageously substituted by an anion selected for the first reactant. This anion is coordinated to the lithium. For example, chlorine is replaced by the NTf2 through an anion exchange with lithium-NTf2 (LiNTf2). The alcohol functional group carried by the first reactant and the halide salt too, the halide of which has been replaced by the NTf2, enables no chelation of the lithium cation. The product obtained is a first reactant for the reaction A of synthesis of the ionic liquid. The product obtained is 99.9% pure.

The method according to the invention uses no lithium and advantageously enables the recycling of the secondary product. Thus it has many advantages and can be used in green chemistry.

EXAMPLE 1: SYNTHESIS OF THE SECOND REACTANT:
1-METHYL-3-METHYLFORMATEIMIDAZOLIUM CHLORIDE

Methyl chloroformate (52 g, 550 mmol) is added dropwise to a solution of 1-methylimidazole (41 g, 500 mmol) in acetonitrile (200 mL) at 0° C. and the reaction lasts for 2 hours. 1-methyl-3-methylformateImidazolium chloride is obtained.

EXAMPLE 2: SYNTHESIS OF THE IONIC LIQUID COMPRISING A CARBONATE FUNCTIONAL GROUP: 1-[2-(METHOXYCARBONYLOXY)ETHYL]-3-METHYLIMIDAZOLIUMBIS(TRIFLUOROMETHANESULFONYL)IMIDE [EMCMLM]TFSI

The first reactant 1-ethanol-3-methylimidazoliumbis(trifluoromethanesulfonyl)imide, (50 g, 122 mmol) and the second reactant as obtained in Example 1: 1-methyl-3-methylformateImidazolium chloride (15.74 g, 111 mmol) are contacted at room temperature for one day. A slightly yellow product is obtained. The ionic liquid having a carbonate functional group is obtained with a yield of about 90%.

EXAMPLE 3: RECYCLING THE SECONDARY PRODUCT INTO THE FIRST REACTANT

One exemplary recycling process is for example described in the International patent application published under number WO2005068404.

The invention claimed is:

1. A method for synthesizing an ionic liquid comprising a carbonate functional group that is not coordinated with lithium, the method comprising reacting without adding lithium a first reactant selected from the group consisting of an imidazolium, a pyrrolidinium and an ammonium and a second reactant being a methyl formate imidazolium, wherein no reactant contains lithium.

2. The method according to claim 1, wherein the first reactant is an imidazolium, a pyrrolidinium or an ammonium alcohol.

3. The method according to claim 1, wherein the first reactant is an imidazolium alcohol, a pyrrolidinium alcohol or an ammonium alcohol salt, the anion of which is bis(trifluoromethanesulfonyl)imide (NTf2).

4. The method according to claim 1, wherein the reacting results in two products, with a main product being an ionic liquid comprising a carbonate functional group and a secondary product being a methyl imidazolium.

5. The method according to claim 4, further comprising recycling, by Hoffmann reaction, the secondary product methyl imidazolium into an imidazolium alcohol, forming the first reactant of the reacting.

6. The method according to claim 5, wherein methyl imidazolium reacts with 2-chloro-1-ethanol to form 1-ethanol-3-methyl imidazolium chloride.

7. The method according to claim 1, wherein the ionic liquid obtained is selected from the group consisting of
- 1-[2-(methoxycarbonyloxy)ethyl]-3-methylimidazolium,
- 1-[2-(ethoxycarbonyloxy)ethyl]-3-methylimidazolium,
- 1-[2-(propoxycarbonyloxy)ethyl]-3-methylimidazolium,
- 1-[2-(isopropoxycarbonyloxy)ethyl]-3-methylimidazolium,
- N-[2-(methoxycarbonyloxy)ethyl]-N'-methylpyrrolidinium,
- N-[2-(ethoxycarbonyloxy)ethyl]-N'-methylpyrrolidinium,
- N-[2-(propoxycarbonyloxy)ethyl]-N'-methylpyrrolidinium,
- N-[2-(isopropoxycarbonyloxy)ethyl]-N'-methylpyrrolidinium,
- N-trimethyl-N-2-[(methoxycarbonyloxy)ethyl]ammonium,
- N-trimethyl-N-2-[(ethoxycarbonyloxy)ethyl]ammonium,
- N-trimethyl-N-2-[(propoxycarbonyloxy)ethyl]ammonium, and
- N-trimethyl-N-2-[(isopropoxycarbonyloxy)ethyl]ammonium, wherein each ionic liquid is associated with a bis(trifluoromethanesulfonyl)imide anion.

8. The method according to claim 1, wherein reacting is executed at ambient temperature in an acetonitrile-based solution in argon atmosphere.

9. The method of claim 1, wherein the second reactant is a chloromethyl formate imidazolium.

10. The method according to claim 9, wherein the second reactant is obtained by a reaction between 1-methylimidazole and methylchloroformate.

11. The method according to claim 10, wherein the reaction is executed at 0° C. in an acetonitrile-based solution for 2 hours.

12. The method according to claim 10, wherein the second reactant obtained by a reaction between 1-methylimidazole and methylchloroformate is directly mixed with the first reactant.

13. The method according to claim 6, wherein the chlorine of 1-ethanol-3-methyl imidazolium chloride is substituted by NTf2 by reaction with lithium bis(trifluoromethanesulfonyl)imide (LiNTf2).

* * * * *